(12) United States Patent
McCarthy et al.

(10) Patent No.: US 11,481,549 B2
(45) Date of Patent: Oct. 25, 2022

(54) DENOVO GENERATION OF MOLECULES USING MANIFOLD TRAVERSAL

(71) Applicant: Accenture Global Solutions Limited, Dublin (IE)

(72) Inventors: Nicholas McCarthy, Dublin (IE); Qurrat Ul Ain, Dublin (IE); Jeremiah Hayes, Dublin (IE); Harshdeep Harshdeep, Dublin (IE)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 394 days.

(21) Appl. No.: 16/884,174

(22) Filed: May 27, 2020

(65) Prior Publication Data

US 2021/0264110 A1 Aug. 26, 2021

Related U.S. Application Data

(60) Provisional application No. 62/979,713, filed on Feb. 21, 2020.

(51) Int. Cl.
*G06F 17/00* (2019.01)
*G06F 40/253* (2020.01)
(Continued)

(52) U.S. Cl.
CPC ........ *G06F 40/253* (2020.01); *G06F 16/2246* (2019.01); *G06F 40/30* (2020.01);
(Continued)

(58) Field of Classification Search
CPC .... G06F 40/253; G06F 16/2246; G06F 40/30; G06N 3/0454; G06N 3/088; G06N 5/003;
(Continued)

(56) References Cited

U.S. PATENT DOCUMENTS

| | | | |
|---|---|---|---|
| 2010/0290480 A1* | 11/2010 | Westphal | H04L 45/14 370/408 |
| 2020/0090049 A1* | 3/2020 | Aliper | G06V 20/69 |
| 2020/0327963 A1* | 10/2020 | Ul Ain | G16C 20/70 |

OTHER PUBLICATIONS

Prykhodko et al., "A de novo molecular generation method using latent vector based generative adversarial network," Journal of Cheminformatics, 2019, 13 pages.

(Continued)

*Primary Examiner* — Charlotte M Baker
(74) *Attorney, Agent, or Firm* — Crowell & Moring LLP

(57) ABSTRACT

The present disclosure relates to systems, methods, and products for identifying candidate molecule. The system includes a non-transitory memory storing instructions; and a processor in communication with the non-transitory memory. The processor executes the instructions to cause the system to receive drug data; convert the drug data into at least one point in a latent space using a grammar variational auto-encoder (VAE) model; receive a query for the at least one candidate molecule; select one or more points in the latent space; and create a k-dimensional tree graph based on the query for the at least one candidate molecule and the selected one or more points; determine a plurality of paths according to an interpolation technique; receive preference data; determine an optimum path; determine at least one candidate point on the optimum path; and determine a drug molecular structure using an inverse of the grammar VAE model.

20 Claims, 8 Drawing Sheets

(51) Int. Cl.
  *G06F 16/22* (2019.01)
  *G06F 40/30* (2020.01)
  *G06N 3/04* (2006.01)
  *G06N 3/08* (2006.01)
  *G06N 5/00* (2006.01)

(52) U.S. Cl.
  CPC ........... *G06N 3/0454* (2013.01); *G06N 3/088* (2013.01); *G06N 5/003* (2013.01)

(58) Field of Classification Search
  CPC ........ G06N 3/08; G06N 5/025; G06N 3/0427; G06N 3/0445; G06N 3/0472; G16C 20/70; G16C 20/50
  USPC ............................................... 704/9; 370/408
  See application file for complete search history.

(56) References Cited

OTHER PUBLICATIONS

Kingma et al., "ADAM: A Method for Stochastic Optimization," 3rd international Conference on Learning Regresentations, ICLR 2015, 15 pages.
Nic Fleming, "Computer-calculated compounds," May 31, 2018, vol. 557, Nature, 3 pages.
Vaswani et al., "Attention is all you need," 31st Conference on Neural Information Processing Systems, CNIPS 2017, Long Beach, CA, 11 pages.
Kingma et al., "Auto-Encoding Variational Bayes," May 1, 2014, 14 pages.
Gomez-Bombarelli et al., "Automatic Chemical Design Using a Data Driver Continuous Representation of Molecules," ACS Central Science, 2018, 9 pages.
Kang et al., "Conditional molecular design with Deep Generative Models," Jul. 23, 2018, 25 pages.
Arus-Pous et al., "Exploring the GDB-13 chemical space using deep generative models," Journal of Cheminformatics, 2019, 14 pages.
Segler et al., "Generating focused molecular libraries for drug discovery with recurrent neural networks," ACS Central Science 4 2018, 12 pages.
Kusner et al., "Grammar Variational Autoencoder," Mar. 6, 2017, 12 pages.
Arvanitidis et al., "Latent Space Oddity: on the Curvature of Deep Generative Models," Jan. 31, 2018, 15 pages.
Maziarka et al., "Mol-Cycle GAN: a generative model for molecular optimization," Journal of Cheminformatics, 2020, 18 pages.
Lim et al., "Molecular generative model based on conditional variational autoencoder for de novo molecular design," Journal of Cheminformatics, 2018, 9 pages.
De Cao et al., "Molgan: an implicit generative model for small molecular graphs," May 30, 2018, 11 pages.
Craig A. James, "Open SMILES specification," www.opensmiles.org, 2016, 38 pages.
Tom White, "Sampling Generative Network," Dec. 6, 2016, 11 pages.
Gaulton et al., "The chembl database in 2017," Nucleic Acids Research, vol. 45, 2017, 10 pages.
Yin Y. Yen, "Finding the k shortest loopless paths in a network," Management Science, vol. 17, No. 11, Accessed Feb. 24, 2009, 6 pages.
Irwin et al., "Zinc: a free tool to discover chemistry for biology," Journal of Chemical Information and Modeling, 2012, 12 pages.
Extended European Search Report in Europe Application No. 21150774.4, dated Jun. 18, 2021, 9 pages.
Harshdeep Singh et al., "ChemoVerse: Manifold traversal of latent spaces for novel molecule discovery", ARXIV.org, Cornell University Library, 201 Olin Library Cornell University Ithaca, NY, 14853, dated Sep. 29, 2020, XP081773729, 5 pages.

* cited by examiner

```
400
```

- obtaining input data, the input data including a set of grammar rules and historical drug data  410
- training a grammar VAE model.  420
- receive drug data  430
- convert the drug data into at least one point in a latent space using a grammar VAE model  440
- receive a query for the at least one candidate molecule  450
- select one or more points in the latent space based on the query for the at least one candidate molecule  460
- create a k-dimensional tree graph based on the query for the at least one candidate molecule and based on the selected one or more points  470
- determine a plurality of paths in the latent space according to an interpolation technique  480
- receive preference data  490
- determine an optimum path from the plurality of paths based on the preference data  492
- determine at least one candidate point on the optimum path  494
- determine a drug molecular structure for each of the at least one candidate point using an inverse of the grammar VAE model  496

DENOVO GENERATION OF MOLECULES USING MANIFOLD TRAVERSAL

CROSS-REFERENCE TO RELATED APPLICATION

This application claims benefit to U.S. Provisional Patent Application No. 62/979,713 filed on Feb. 21, 2020, the entirety of which is incorporated by reference herein.

TECHNICAL FIELD

This disclosure relates in general to the fields of bioinformatics, computational chemistry and drug discovery using latent space exploration.

BACKGROUND

Basic techniques and equipment for ranking drug compounds, scoring gene expressions and enrichment pathways, and selecting predictive biomarkers are known in the art. Both drug data and biological data have features that can be described as discrete values using variational auto-encoders to generate latent spaces for modeling the probability metrics distributions of latent variables that may be explored using interpolation methods and quantitative structure-activity relationship models. While various technologies have used either drug data or biological data independently to generate latent space, a multi-modal latent space based on the combination of drug molecular-structure data and biological-treatment data is desired to more efficiently identify optimal and/or new drug compounds for the treatment of diseases.

SUMMARY

The present disclosure describes a system including a non-transitory memory storing instructions executable to identify at least one candidate molecule; and a processor in communication with the non-transitory memory. The processor executes the instructions to cause the system to receive drug data; convert the drug data into at least one point in a latent space using a grammar variational auto-encoder (VAE) model; receive a query for the at least one candidate molecule; select one or more points in the latent space based on the query for the at least one candidate molecule; and create a k-dimensional tree graph based on the query for the at least one candidate molecule and based on the selected one or more points. The processor executes the instructions to further cause the system to determine a plurality of paths in the latent space according to an interpolation technique; receive preference data; determine an optimum path from the plurality of paths based on the preference data; determine at least one candidate point on the optimum path; and determine a drug molecular structure for each of the at least one candidate point using an inverse of the grammar VAE model.

The present disclosure describes a method includes receiving, by a device, drug data. The device includes a memory storing instructions for use in identifying at least one candidate molecule and a processor in communication with the memory. The method includes converting, by the device, the drug data into at least one point in a latent space using a grammar variational auto-encoder (VAE) model; receiving, by the device, a query for the at least one candidate molecule; selecting, by the device, one or more points in the latent space based on the query for the at least one candidate molecule. The method further includes creating, by the device, a k-dimensional tree graph based on the query for the at least one candidate molecule and based on the selected one or more points; determining, by the device, a plurality of paths in the latent space according to an interpolation technique; receiving, by the device, preference data; determining, by the device, an optimum path from the plurality of paths based on the preference data; determining, by the device, at least one candidate point on the optimum path; and determining, by the device, a drug molecular structure for each of the at least one candidate point using an inverse of the grammar VAE model.

The present disclosure describes a product including machine-readable media other than a transitory signal; and instructions stored on the machine-readable media for identify at least one candidate molecule. When a processor executes the instructions, the product is configured to cause the processor to receive drug data; convert the drug data into at least one point in a latent space using a grammar variational auto-encoder (VAE) model; receive a query for the at least one candidate molecule; and select one or more points in the latent space based on the query for the at least one candidate molecule. When the processor executes the instructions, the product is configured to cause the processor to create a k-dimensional tree graph based on the query for the at least one candidate molecule and based on the selected one or more points; determine a plurality of paths in the latent space according to an interpolation technique; receive preference data; determine an optimum path from the plurality of paths based on the preference data; determine at least one candidate point on the optimum path; and determine a drug molecular structure for each of the at least one candidate point using an inverse of the grammar VAE model.

BRIEF DESCRIPTION OF THE DRAWINGS

FIG. 4 shows a flow diagram of an embodiment of a method for identifying at least one candidate molecule.

DETAILED DESCRIPTION

Figure 1:
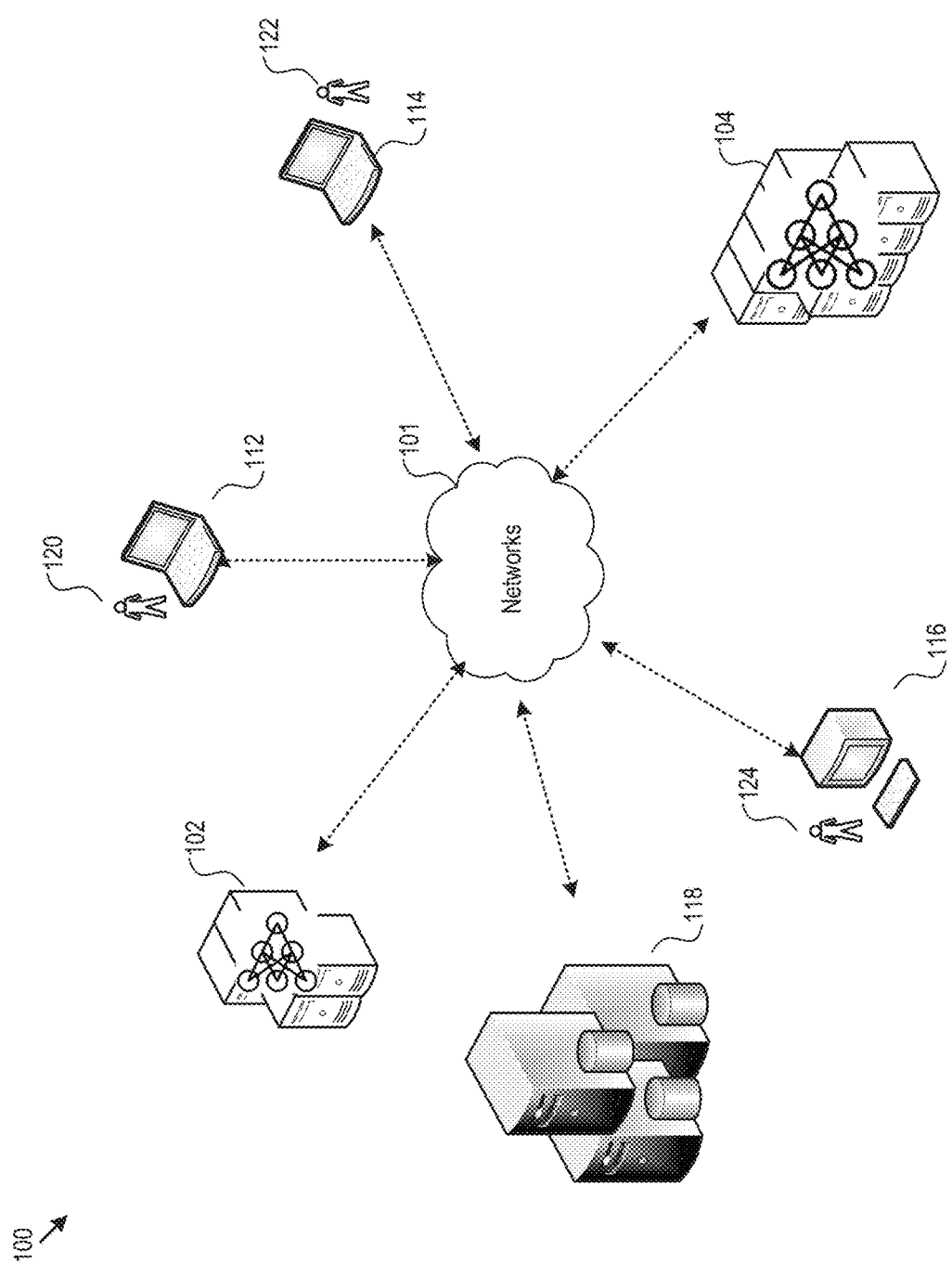
FIG. 1 shows an exemplary electronic communication environment for identifying at least one candidate molecule.

The disclosure will now be described in detail hereinafter with reference to the accompanied drawings, which form a part of the present disclosure, and which show, by way of illustration, specific examples of embodiments. Please note that the disclosure may, however, be embodied in a variety of different forms and, therefore, the covered or claimed subject matter is intended to be construed as not being limited to any of the embodiments to be set forth below. Please also note that the disclosure may be embodied as methods, devices, components, or systems. Accordingly, embodiments of the disclosure may, for example, take the form of hardware, software, firmware or any combination thereof.

Throughout the specification and claims, terms may have nuanced meanings suggested or implied in context beyond an explicitly stated meaning. Likewise, the phrase "in one embodiment" or "in one implementation" as used herein does not necessarily refer to the same embodiment or implementation and the phrase "in another embodiment" or "in another implementation" as used herein does not necessarily refer to a different embodiment or implementation. It is intended, for example, that claimed subject matter includes combinations of exemplary embodiments or implementations in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

In order to design a more potent, effective, and targeted chemical entity, it may be important to identify molecular structures with the desired chemical properties. Recent advances in generative models using neural networks and machine learning have been widely used in this domain to design virtual libraries of drug-like compounds. These models may help to rapidly produce novel molecular structures. Various challenges and problems may exist with these models in intelligent exploration of the latent spaces of generative models, thereby reducing the randomness in the generative procedure.

The present disclosure describes varies embodiments of methods, apparatus, and products of identifying at least one candidate molecule, including DeNovo generation of molecules using manifold traversal, to address at least one of the challenges and problems discussed above. The embodiments in the present disclosure may be used to discover new chemical molecules that may be used as drugs for diseases.

The present disclosure describes embodiments of a manifold traversal with heuristic search to explore the latent chemical space using different heuristics and scores. The latent chemical space may be generated by various models with one of them being Grammar variational auto-encoder (VAE). In some embodiments, an addition of an attention layer in a recurrent neural network (RNN) decoder layer of grammar VAE may significantly improves the semantic validity of generated molecules. In some embodiments, in a path finding algorithm, path distance may be weighted by more than one expert-defined heuristic, for example, a quantitative estimate of drug-likeness (QED), synthetic accessibility, molecular similarity, etc.

FIG. 1 shows an exemplary electronic communication environment 100 in which one or more embodiments of identifying at least one molecules may be implemented. The electronic communication environment 100 may include one or more servers (102 and 104) implementing the embodiment of DeNovo generation of molecules using manifold traversal, one or more user devices (112, 114, and 116) associated with users (120, 122, and 124), and one or more databases 118, in communication with each other via public or private communication networks 101.

The server 102 may be implemented as a central server or a plurality of servers distributed in the communication networks. While the server 102 shown in FIG. 1 is implemented as a single server, the server 102 may be implemented as a group of distributed servers, or may be distributed on the server 104.

The user devices 112, 114, and 116 may be any form of mobile or fixed electronic devices including but not limited to desktop personal computer, laptop computers, tablets, mobile phones, personal digital assistants, and the like. The user devices 112, 114, and 116 may be installed with a user interface for accessing the embodiment of DeNovo generation of molecules using manifold traversal. The one or more database 118 of FIG. 1 may be hosted in a central database server, a plurality of distributed database servers, or in cloud-based database hosts. The database 118 may be organized and implemented in any form, including but not limited to relational database containing data tables, graphic database containing nodes and relationships, and the like. The database 118 may be configured to store the intermediate data and/or final results for implementing the embodiment of DeNovo generation of molecules using manifold traversal.

Figure 2:
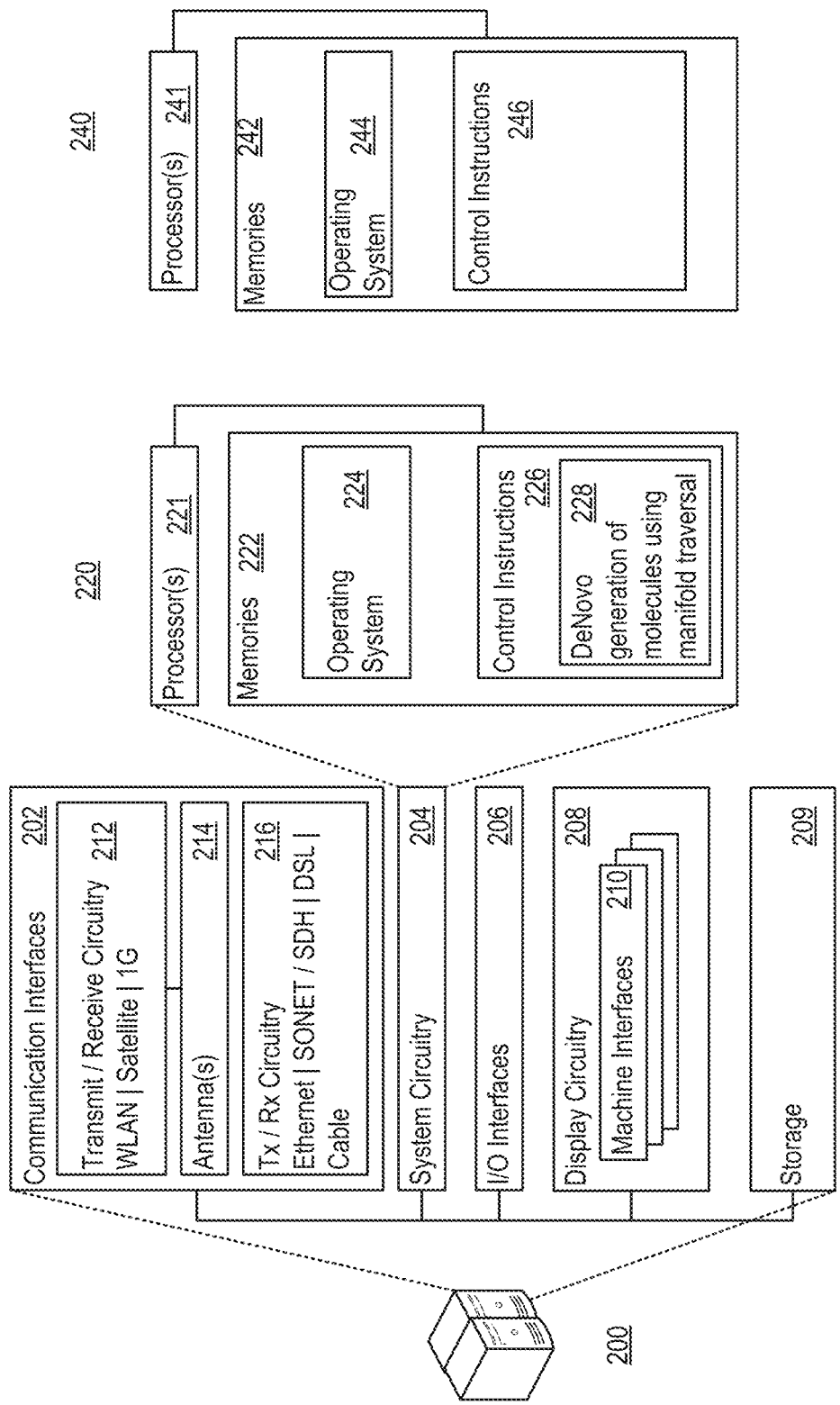
FIG. 2 shows computer systems that may be used to implement various components of the electronic communication environment of FIG. 1.

FIG. 2 shows an exemplary system, which is a computer system 200 for implementing the server 102, or the user devices 112, 114, and 116. The computer system 200 may include communication interfaces 202, system circuitry 204, input/output (I/O) interfaces 206, storage 209, and display circuitry 208 that generates machine interfaces 210 locally or for remote display, e.g., in a web browser running on a local or remote machine. The machine interfaces 210 and the I/O interfaces 206 may include GUIs, touch sensitive displays, voice or facial recognition inputs, buttons, switches, speakers and other user interface elements. Additional examples of the I/O interfaces 206 include microphones, video and still image cameras, headset and microphone input/output jacks, Universal Serial Bus (USB) connectors, memory card slots, and other types of inputs. The I/O interfaces 206 may further include magnetic or optical media interfaces (e.g., a CDROM or DVD drive), serial and parallel bus interfaces, and keyboard and mouse interfaces.

The communication interfaces 202 may include wireless transmitters and receivers ("transceivers") 212 and any antennas 214 used by the transmitting and receiving circuitry of the transceivers 212. The transceivers 212 and antennas 214 may support Wi-Fi network communications, for instance, under any version of IEEE 802.11, e.g., 802.11n or 802.11ac. The communication interfaces 202 may also include wireline transceivers 216. The wireline transceivers 116 may provide physical layer interfaces for any of a wide range of communication protocols, such as any type of Ethernet, data over cable service interface specification (DOCSIS), digital subscriber line (DSL), Synchronous Optical Network (SONET), or other protocol.

The storage 209 may be used to store various initial, intermediate, or final data or model for implementing the embodiment of DeNovo generation of molecules using manifold traversal. These data corpus may alternatively be stored in the database 118 of FIG. 1. In one implementation, the storage 209 of the computer system 200 may be integral with the database 118 of FIG. 1. The storage 209 may be centralized or distributed, and may be local or remote to the computer system 200. For example, the storage 209 may be hosted remotely by a cloud computing service provider.

The system circuitry 204 may include hardware, software, firmware, or other circuitry in any combination. The system circuitry 204 may be implemented, for example, with one or more systems on a chip (SoC), application specific integrated circuits (ASIC), microprocessors, discrete analog and digital circuits, and other circuitry.

For example, at least some of the system circuitry 204 may be implemented as processing circuitry 220 for the server 102 in FIG. 1. The processing circuitry 220 may include one or more processors 221 and memories 222. The memories 222 stores, for example, control instructions 226 and an operating system 224. The control instructions 226, for example may include instructions for implementing the components 228 of the embodiment of DeNovo generation of molecules using manifold traversal. In one implementation, the instruction processors 221 execute the control instructions 226 and the operating system 224 to carry out any desired functionality related to the embodiment of DeNovo generation of molecules using manifold traversal.

Alternatively, or in addition, at least some of the system circuitry 204 may be implemented as client circuitry 240 for the user devices 112, 114, and 116 of FIG. 1. The client circuitry 240 of the user devices may include one or more instruction processors 241 and memories 242. The memories 242 stores, for example, control instructions 246 and an operating system 244. In one implementation, the instruction processors 241 execute the control instructions 246 and the operating system 244 to carry out any desired functionality related to the user devices.

Designing a new effective chemical entity is a time consuming and error prone task. For example, pharmaceutical companies spend billions of dollars into screening vast libraries of chemical compounds for hit and lead identification. Neural networks and machine learning may be used to design virtual libraries of drug-like compounds. These computational models may have the ability to optimize the chemical properties of compounds in vector space and generate novel chemical structures. There are some problems and issues with some computational models, for example, challenges in the intelligent exploration of the latent spaces of generative models reducing randomness in the generative procedure.

The present disclosure describes a system for identifying one or more candidate molecules efficiently, addressing at least some of the drawbacks as discussed above. Identifying molecular structures with desired chemical properties may be used to design a more potent, effective, and targeted chemical entity. The present disclosure describes a manifold traversal with heuristic search to explore the latent chemical space. Different heuristics and scores, for example but not limited to, Tanimoto coefficient, synthetic accessibility, binding activity, or quantitative estimate of drug-likeness (QED), may be incorporated to increase the validity and proximity for desired molecular properties of the generated molecules. The present disclosure describes embodiments of producing latent chemical spaces via various generative models. The generative models may include a grammar variational autoencoder (VAE) with self-attention that enforces chemical context and deals with the randomized generation and validity of simplified molecular-input line-entry system (SMILES).

To generate molecules, recurrent neural networks (RNN) with long-short-term memory (LSTM) units may be used to generate SMILES representations of new compounds. SMILES may be used as input strings and text generation models may be given the task of encoding and de-coding the SMILES string directly. Various VAEs may be used to generate molecules.

Figure 3:
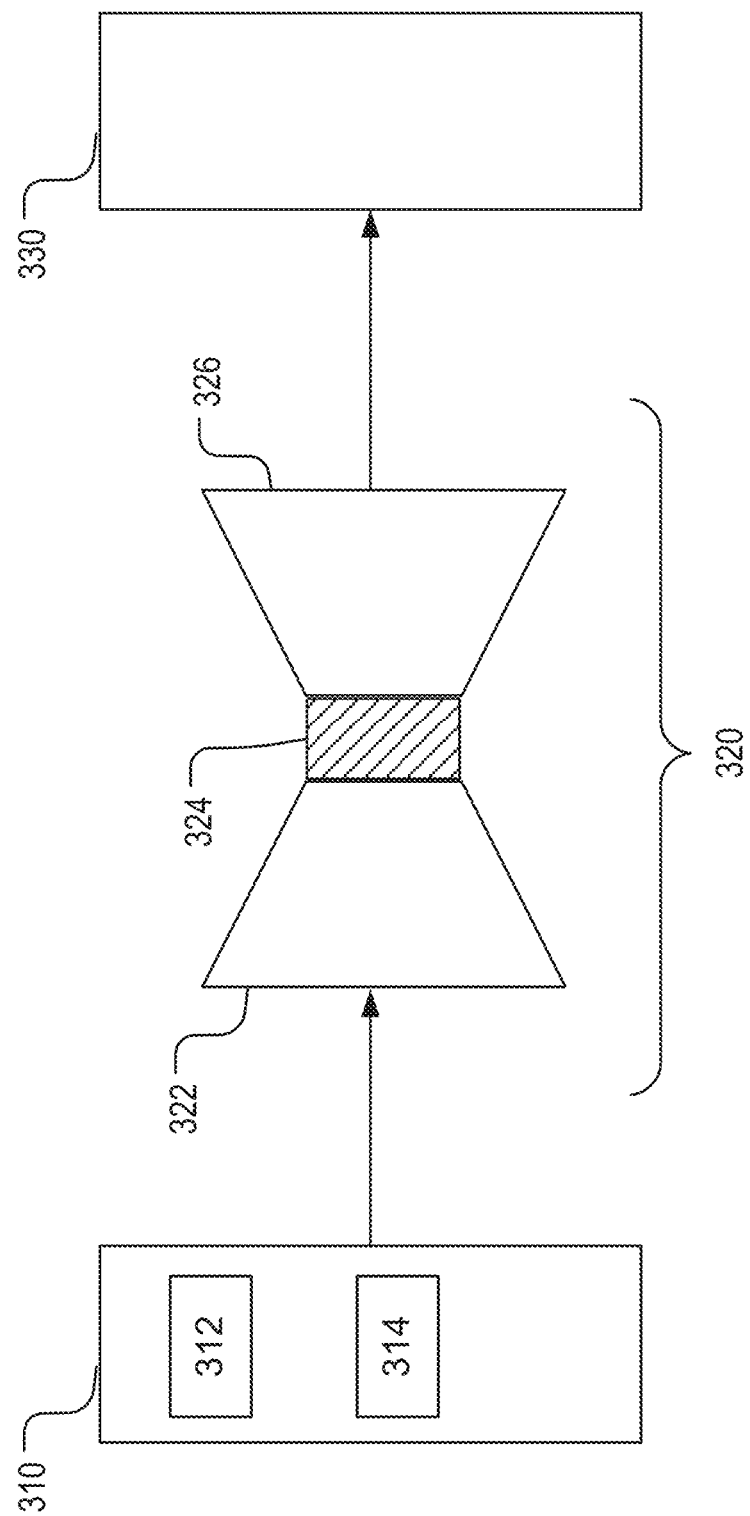
FIG. 3 shows a schematic diagram for some embodiment of identifying at least one candidate molecule.

FIG. 3 shows a schematic diagram of an embodiment of a system for identifying at least one candidate molecule. The system 300 may include a VAE 320, an input 310, and an output 330.

The VAE 320 may be a neural network including an encoder 322 that transforms a compound's representation into a compressed latent space 324, and a decoder 326 that generates compounds from the latent space. The VAE 320 may include a conditional variational autoencoders (CVAE) which facilitates generation of new molecules with desired molecular properties by incorporating the molecular properties of a compound into the encoder layer and helping in the generation of more drug-like molecules. Generative adversarial networks (GANs) may be implemented in the similar manner and may be combined with reinforcement learning and graph representation of molecules to optimize the generation of molecules with specified molecular properties. In one implementation, the encoder 322 may include a convolutional neural network (CNN). In another implementation, the decoder 326 may include a recurrent layer (for example, a Long-short-term memory (LSTM) or a gated recurrent unit (GRU)) with attention.

In various embodiments, the VAE 320 may include a grammar VAE. The grammar VAE 320 may perform as a generative model for producing the latent space 324, and a manifold traversal method for interpolation of this latent space to design novel and optimized molecules. This combination of generation and exploration of latent space may design novel molecules and explore regions of chemical space where more potent chemical compounds may exist.

The input 310 may include a set of grammars 312 and a dataset of molecules 314. In one implementation, the set of grammars 312 may include a set of SMILES grammar specification. The output 330 may receive molecules decoded to one-hot encoding according to production rules and visualize the molecules and/or the molecular structures on a user interface. A set of grammars may be called as a grammar including one or more grammatical rules.

In various embodiments, molecules may be represented using a simplified molecular-input line-entry system (SMILES) string. For example, Aspirin (Acetylsalicylic Acid) may be represented by a SMILES string of CC(=O) OC1=CC=CC=C1C(=O)O. SMILES has a grammar that defines syntactically valid strings, and semantic structure may be defined elsewhere. In some implementations, the grammar may specify how ring bonds are written, but does not ensure that they always come in pairs.

For example, open SMILES grammars may include one or more the following:
Smiles:=chain;
Chain:=branched_atom\chain branched_atom\chain bond branched_atom\chain dot branched_atom;

Branched-atom:=atom ringbond* branch*; and
Ring bond:=bond? Digit\bond? % DIGIT DIGIT.

In various embodiments, the VAE 320 may include a class of generative models that produces a latent space whose encoded distribution may be traversed, such that generating a new sample that is close to the latent encoding of a known sample may be similar to the known sample. In some implementation, a grammar VAE may be used to generate samples with a discrete structure, e.g. molecules, arithmetic expressions, etc. Samples generated like this may be syntactically valid with respect to the specified grammar used in training the generator. Various methods such as nearest neighbor and different manifold search strategies may be used to generate samples from a latent space with specific properties.

In various embodiments, a manifold traversal method may be applied based on points in the generated latent space to generate molecules from the latent space with desired properties. Linear and spherical interpolation may be used as common approaches. These common approaches may assume that the latent space is Euclidean and flattened out, which may provide a distorted view. The manifold traversal may provide choices of path exploration on various conditions, addressing some of the drawbacks discussed above.

In the manifold traversal method, a source point and a destination point may be selected in the latent space. In one implementation, the source point and the destination point may correspond to single molecules encoded in the latent space. In another implementation, the source point and the target point may be centroids/medoids of a cluster of molecules labeled with a desired property. For example, a cluster of molecules used in treating a specific illness condition, including, asthma, diabetes, or the like.

Interpolation may be implemented by calculating Jacobian matrix corresponding to first order derivative of change for all points of interest, and building a k-d tree over the resulting distances. The method may receive user preference data including domain-specific heuristics such as fingerprint similarity, synthetic accessibility, absolute difference of drug-likeliness, or the like. The method may further determine an optimum path from the source to destination points on the k-dimensional (k-d) tree based on the preference data.

Referring to FIG. 4, the present disclosure describe various embodiments of a method 400 of DeNovo generation of molecules using manifold traversal. The method 400 may include a portion or all of the following steps.

Referring to step 410, the method 400 may include obtaining input data, the input data including a set of grammar rules and historical drug data. The historical drug data may include historical drug molecular structure data in a simplified molecular-input line-entry system (SMILES) data format. The set of grammar rules may include a set of SMILES grammar specifications.

Figure 5:
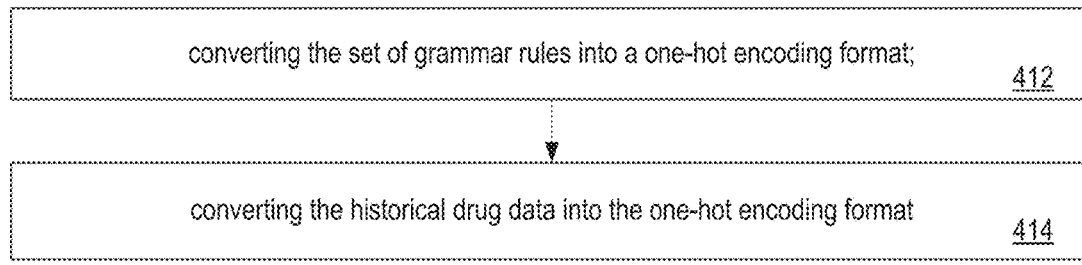
FIG. 5 shows a flow diagram of an embodiment of a step in the method in FIG. 4.

Referring to FIG. 5, in various implementations, the step 410 may further include a portion or all of the following steps: step 412, converting the set of grammar rules into a one-hot encoding format; and step 414, converting the historical drug data into the one-hot encoding format.

Figure 6A:
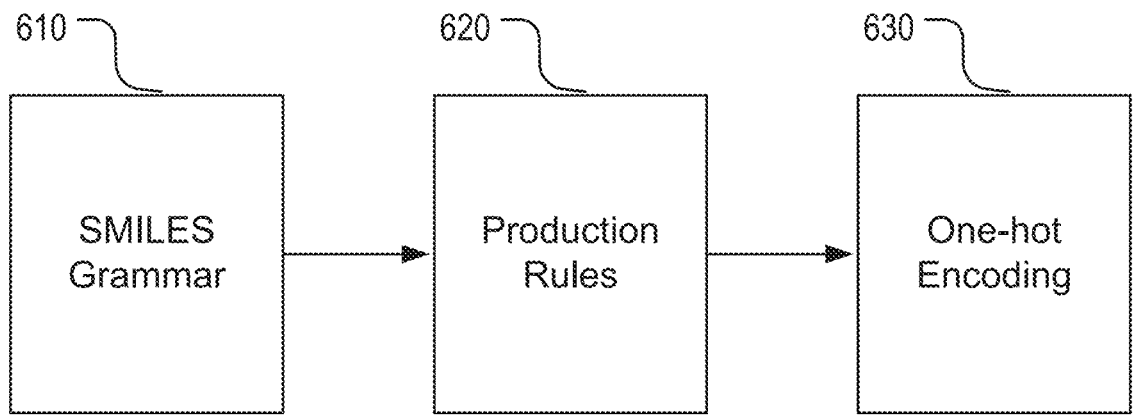
FIG. 6A shows a schematic diagram for some embodiments of converting a set of grammar rules into a one-hot encoding format.
Figure 6B:
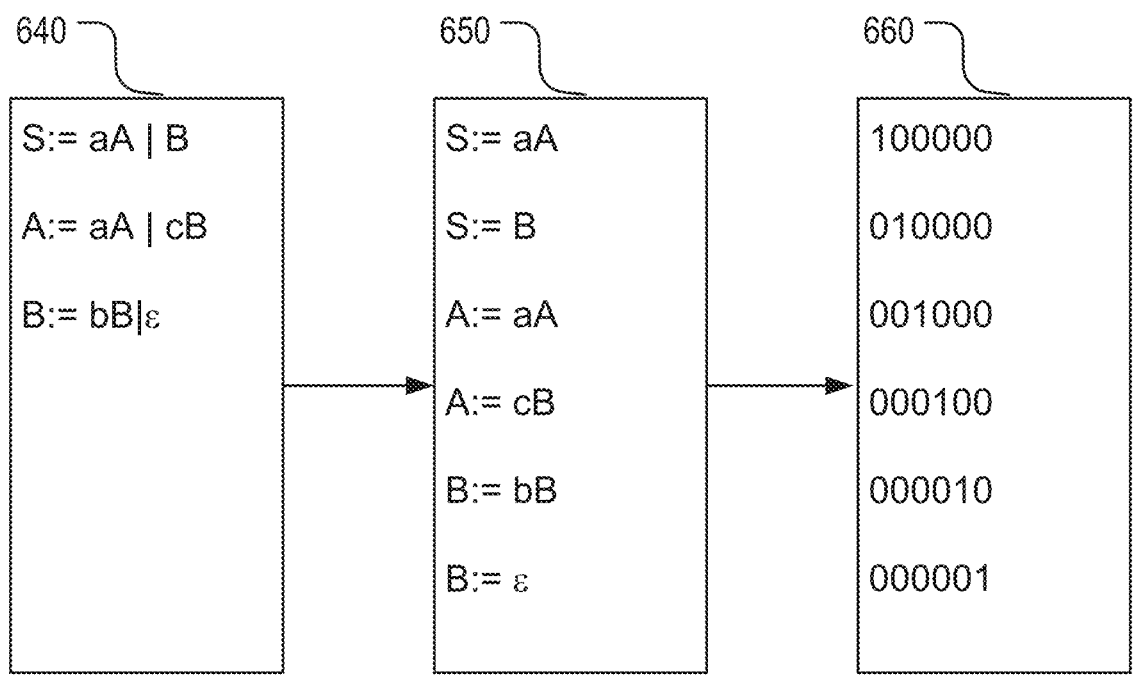
FIG. 6B shows a schematic diagram for an exemplary embodiment of converting a set of grammar rules into a one-hot encoding format.

Referring to step 412, the method 400 may include converting the set of grammar rules into a one-hot encoding format. Referring to FIG. 6A, the method may including converting the set of grammar including a set of SMILES grammar 610 to a set of production rules 620, which is converted to a set of one-hot encoding 630. Each of the one-hot encoding may correspond to each of the production rule in the SMILES grammar. FIG. 6B shows an example of converting the set of grammar 640 to one-hot encoding 660 of each production rule 650 in the grammar.

Figure 7A:
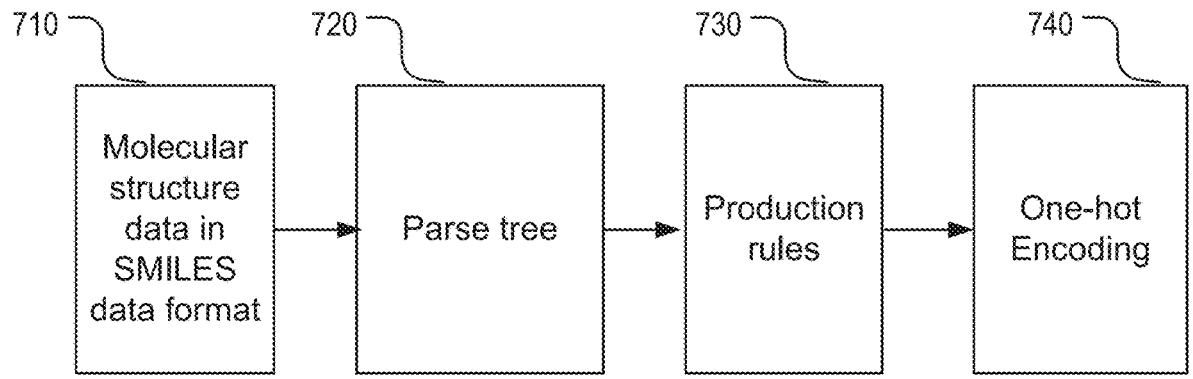
FIG. 7A shows a schematic diagram for some embodiments of converting molecules in simplified molecular-input line-entry system (SMILES) data format into the one-hot encoding format.
Figure 7B:
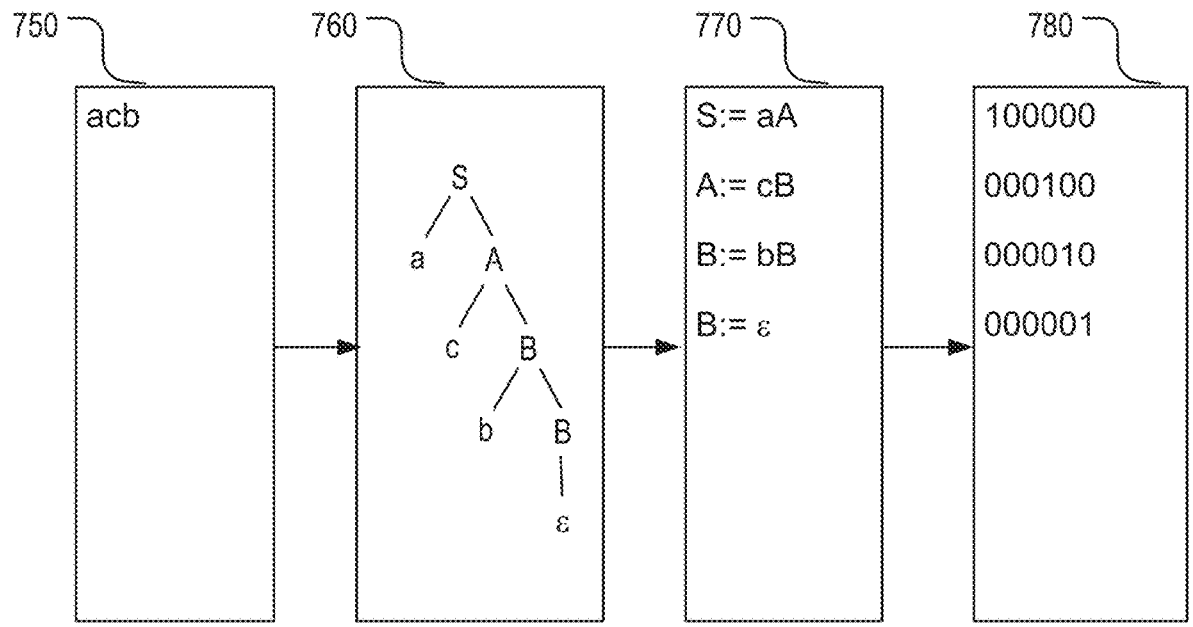
FIG. 7B shows a schematic diagram for an exemplary embodiment of converting molecules in SMILES data format into the one-hot encoding format.

Referring to step 414, the method 400 may include converting the historical drug data into the one-hot encoding format. Referring to FIG. 7A, the method may including converting molecular structure data in SMILES data format 710 to a parse tree based on the set of production rules corresponding to SMILES grammar; converting the parse tree 720 to a corresponding production rules 730; and converting the corresponding production rules 730 to the one-hot encoding format 740 for the molecular structure data. FIG. 7B shows an example of converting molecular structure data in SMILES data format 750 into the one-hot encoding format 780 via corresponding parse tree 760 and corresponding production rules 770.

Referring to step 420 in FIG. 4, the method 400 may include training a grammar VAE artificial intelligence (AI) model based on the input data. In one implementation, the grammar VAE model may include the VAE model in FIG. 3. In another implementation, the method may further include training the grammar VAE model based on the set of grammar rules in the one-hot encoding format and the historical drug molecular structure data in the one-hot encoding format. In some implementations, the method 400 may further include adding one or more attention layers in the RNN decoder in grammar VAE AI model, which may significantly improve semantic validity of decoded molecules. The one or more attention layers improve semantic validity of decoded molecules by allowing the model to pay attention to the entire sequence of inputs, rather than using just the final hidden state of an LSTM or GRU encoder. The SMILES is a context free grammar, and an internal memory state may be required to remember rule branches for closure, traditionally achieved by using a push-down automata which uses a stack data-structure to 'remember'—analogously, using attention allows the network to remember which rules are on the stack. This significantly may improve results for cases where the decoder may forget which rule is being decoded, most notably when matching ringbond pairs.

Referring to step 430, the method 400 may include receiving drug data. The drug data may include drug molecular structure data in a SMILES data format. In one implementation, the drug data may be drug data including drug molecular structure data in the SMILES data format.

Referring to step 440, the method 400 may include converting the drug data into at least one point in a latent space using the grammar VAE model. In various implementation, the method may further include annotating known compounds in a latent space with target labels (i.e. disease target, property, etc.)

Referring to step 450 in FIG. 4, the method 400 may include receiving a query for the at least one candidate molecule. In various implementations, the query for the candidate molecule may include at least one query of a drug molecular structure query, and/or a drug treatment query, and/or a drug effect query.

Referring to step 460, the method 400 may include selecting one or more points in the latent space based on the query for the at least one candidate molecule. In one implementation, one selected point in the latent space may be a centroid/medoid of a first target label cluster, and another selected point in the latent space may be a centroid/medoid of a second target label cluster. For example, a first target label cluster may be a cluster of molecules for treating asthma; and a second target label cluster may be a cluster of molecules for treating diabetes.

Referring to step 470, the method 400 may include creating a k-dimensional (k-d) tree graph based on the query for the at least one candidate molecule and based on the selected one or more points. Referring to step 480, the method 400 may include determining a plurality of paths in the latent space according to a Riemannian interpolation technique. In one implementation, upon picking centroid/medoid of target label clusters, n points close to the cluster centroid/medoid may be selected. In another implementation, n equidistant points at radius r from centroid/medoid may be selected. The k-d tree graph may be created based on the corresponding n points.

In various implementations, the k-d tree may be constructed based path distance $J_{ij}$ between two points i and j. The path distance may be obtained by Riemannian interpolation.

In one implementation, the path distance may be calculated by the following steps.

1. For a starting cluster (for example, a cluster of molecules for treating asthma) and an ending cluster (for example, a cluster of molecules for treating diabetes), $C_1$ represents a centroid of the starting cluster, and $C_2$ represents a centroid of the end cluster. Initially, let $i=C_1$.

2. For each starting point i, creating k-d tree based on the starting point and find the k nearest points in the neighborhood→$N_i$.

3. Constructing a linear function between i and all points j∈$N_i$.

4. Calculating Jacobian matrix. Each element $J_{ij}$ of the Jacobian matrix may be represented by:

$$J_{ij} = \frac{\partial dec(L_{ij})}{\partial L_{ij}},$$

wherein $L_{ij}$ is the line in latent space from point i to point j; dec( ) is the decoder output with respect to the latent space (L), which may measure differences (for example, stretching, rotation, transformation) for each axis in the output space with respect to the latent space.

5. Finding the $J_{ij}$ that minimizes $\sqrt{(C_i-C_2)J_{ij}(C_i-C_2)^T}$, where T is the transpose of a matrix, to determine a correct direction has been selected.

6. Repeating step 2 for each point added to the candidate set, until all labeled points are mapped.

Optionally and alternatively, in another implementation, the path distance may be calculated by the following steps.

1. For a source point s and a destination point d in latent space L, selecting, initially, i=s.

2. For each point i, creating k-d tree and finding n nearest neighbors of i→$N_i$.

3. Calculating Jacobian matrix element of decoder output with respect to the latent space by:

$$J_{ij} = \frac{\partial dec(L_{ij})}{\partial L_{ij}},$$

wherein $L_{ij}$ is the line in latent space from point i to point j; dec( ) is the decoder output with respect to the latent space (L).

4. Obtaining k heuristic distances $H_{ij}^k$.

5. Determining path weight $P_{ij}$ based on $\Sigma_{ij}^N J_{ij} + \Sigma_k H_{ij}^k \cdot W^k$, where $W^k$ is the weights associated with the k heuristics; and storing the path weights in the k-d tree.

6. Repeating step 2 for each point added to the candidate set, until all labeled points are mapped.

Referring to step 490, the method 400 may include receiving preference data. In one implementation, preference data may include one or more expert-defined heuristics, e.g. synthetic accessibility, molecular similarity, quantitative estimate of drug-likeness (QED), etc. The Path distances may be weighted by the one or more expert-defined heuristics in the preference data.

Referring to step 492, the method 400 may include determine an optimum path from the plurality of paths based on the preference data. In various implementation, a path finding algorithm (e.g. A* search, Yen's algorithm [Yen, 1971] Jin Y Yen. Finding the k shortest loopless paths in a network. management Science, 17(11):712-716, 1971) may be used to traverse the k-d tree to determine the optimum path.

Referring to step 494, the method 400 may include determining at least one candidate point on the optimum path. In one implementation, n points along the optimum path may be obtained. The N points may be evenly distributed along the optimum path as equidistant points.

Referring to step 496, the method 400 may include determine a drug molecular structure for each of the at least one candidate point using an inverse of the grammar VAE model. For each of the at least one candidate point on the optimum path, a corresponding molecule may be decoded based on its latent space representation.

Figure 8:
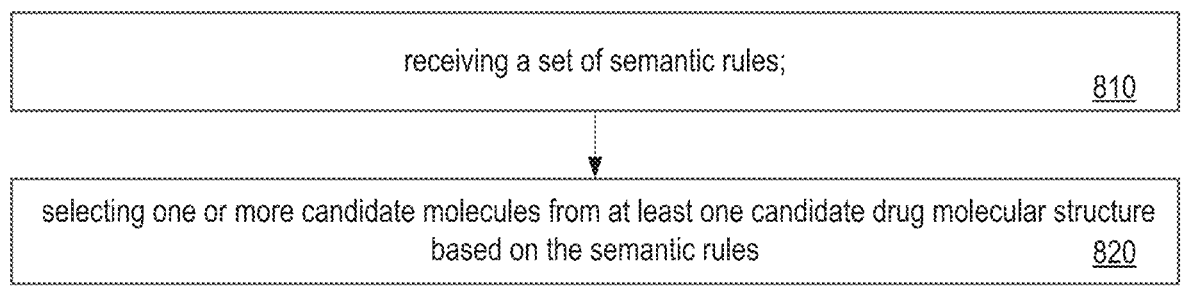
FIG. 8 shows a flow diagram of an embodiment of a method for identifying at least one candidate molecule.

Referring to FIG. 8, the method 400 may further include step 810: receiving a set of semantic rules; and step 820: selecting one or more candidate molecules from at least one candidate drug molecular structures based on the semantic rules.

The present disclosure describes one exemplary embodiment for identifying at least one candidate molecule. The exemplary embodiment uses 250,000 molecules from the publicly available ZINC database and 100,000 drawn from the publicly available ChEMBL database, both of which include commercially available drug molecules. Each molecule is represented as a SMILES string, and is further processed into either a one-hot character encoding or a set of context free grammar (CFG) rules. Grammar rules are obtained from the OpenSMILES specification, which denotes how the SMILES representation was formed based on the rules. OpenSMILES CFG consists of 76 rules, to which an additional 7 are added, and 9 modified in order to represent the more complex ChEMBL dataset.

The exemplary embodiment implements three models: a first model includes a VAE, a second model includes a grammar VAE, and a third model includes a grammar VAE with self-attention. The exemplary embodiment may be modular, extensible and efficient, in which any other encoder-decoder architecture model may be implemented to generate a latent space.

The ChEMBL dataset may be less standardized and contains more complex molecules, so transfer learning is performed by initially training each model on the ZINC dataset for 50 epochs with the Adam optimizer. A learning rate scheduler is instantiated after 15 epochs with a factor of 0.1 (initialized at 0.001) and then is trained on the ChEMBL dataset for 50 epochs, producing a 56-dimensional latent space. The encoder is comprised of 3 convolutional 1D layers of size 9, 10, 11 filter respectively, while the decoder is comprised 3 gated recurrent units (GRU) of 501 units.

The exemplary embodiment demonstrates the manifold traversal may have a much higher rate of valid decoded molecules. For example, when considering the centroids of molecules treating diabetes and lung cancer, linear interpolation with 100 equidistant points decoded along the path generated just 3 compounds with valid structures. Yen's algorithm and manifold traversal method, with perturbing the source and destination points, produce 4 different paths generated 44, 1, 68 and 43 valid compounds respectively.

The exemplary embodiment may visualize the different paths on the user interface, using a test set of 282 diabetes (149) and lung cancer (133) compounds. The user interface may show a k-d tree generated by algorithm 1. By hovering over a node, the user interface may show the molecular structure and corresponding fingerprint similarity. The user interface may show different paths generated by the algorithm, including the new and valid molecules discovered while exploring each path. The user interface may also show the corresponding histograms for synthetic accessibility and activity scores to compare different paths. Upon clicking by an operator, the user interface may expand key information about each newly discovered compound on the path, such as molecular weight, total number of rings, atoms etc.

The present disclosure describes embodiments of a model-agnostic platform for performing manifold traversal of generated latent spaces with user specified heuristics. The present disclosure may capture more context on which model has been learnt. Methods for exploration of latent spaces generated from millions of molecules provide an extremely valuable tool for virtual drug screening and its ability to facilitate rapid drug discovery. The present disclosure may also be used for implementation of additional models to produce latent-spaces with varied characteristics, latent-space evaluation metrics, and more sophisticated methods for curve fitting in high dimensional spaces such as Bezier curves and Gaussian regression.

The methods, devices, processing, and logic described above may be implemented in many different ways and in many different combinations of hardware and software. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

While the particular disclosure has been described with reference to illustrative embodiments, this description is not meant to be limiting. Various modifications of the illustrative embodiments and additional embodiments of the disclosure will be apparent to one of ordinary skill in the art from this description. Those skilled in the art will readily recognize that these and various other modifications can be made to the exemplary embodiments, illustrated and described herein, without departing from the spirit and scope of the present disclosure. It is therefore contemplated that the appended claims will cover any such modifications and alternate embodiments. Certain proportions within the illustrations may be exaggerated, while other proportions may be minimized. Accordingly, the disclosure and the figures are to be regarded as illustrative rather than restrictive.

What is claimed is:

1. A system comprising:
a non-transitory memory storing instructions executable to identify at least one candidate molecule; and
a processor in communication with the non-transitory memory, wherein, the processor executes the instructions to cause the system to:
receive drug data;
convert the drug data into at least one point in a latent space using a grammar variational auto-encoder (VAE) model;
receive a query for the at least one candidate molecule;
select one or more points in the latent space based on the query for the at least one candidate molecule;
create a k-dimensional tree graph based on the query for the at least one candidate molecule and based on the selected one or more points;
determine a plurality of paths in the latent space according to an interpolation technique;
receive preference data;
determine an optimum path from the plurality of paths based on the preference data;
determine at least one candidate point on the optimum path; and
determine a drug molecular structure for each of the at least one candidate point using an inverse of the grammar VAE model.

2. The system according to claim 1, wherein the processor executes the instructions to further cause the system to:
obtain input data, the input data comprising a set of grammar rules and historical drug data; and
train the grammar VAE model based on the input data.

3. The system according to claim 2, wherein:
the historical drug data comprises historical drug molecular structure data in a simplified molecular-input line-entry system (SMILES) data format;

the processor executes the instructions to further cause the system to:
   convert the set of grammar rules into a one-hot encoding format, and
   convert the historical drug data into the one-hot encoding format; and
when the processor executes the instructions to cause the system to train the grammar VAE model based on the input data, the processor executes the instructions to cause the system to:
   train the grammar VAE model based on the set of grammar rules in the one-hot encoding format and the historical drug molecular structure data in the one-hot encoding format.

4. The system according to claim 1, wherein:
the drug data comprises drug molecular structure data in a SMILES data format; and
the preference data comprises at least one expert-defined heuristics to be used to weight at least one path distance in the k-dimensional tree graph.

5. The system according to claim 1, wherein:
the query for the candidate molecule comprises a drug molecular structure query, and/or a drug treatment query, and/or a drug effect query.

6. The system according to claim 5, wherein, when the processor executes the instructions to cause the system to select the one or more points in the latent space based on the query for the candidate molecule, the processor executes the instructions to cause the system to:
   select a first point in the latent space based on the drug treatment query according to a centroid algorithm;
   select a second point in the latent space based on the drug molecular structure query according to a centroid algorithm; and
   determine a plurality of paths between the first point and the second point in the latent space according to a Riemannian interpolation technique.

7. The system according to claim 1, wherein the processor executes the instructions to further cause the system to:
   receive a set of semantic rules; and
   select one or more candidate molecules from at least one candidate drug molecular structure based on the semantic rules.

8. A method comprising:
receiving, by a device comprising a memory storing instructions for use in identifying at least one candidate molecule and a processor in communication with the memory, drug data;
converting, by the device, the drug data into at least one point in a latent space using a grammar variational auto-encoder (VAE) model;
receiving, by the device, a query for the at least one candidate molecule;
selecting, by the device, one or more points in the latent space based on the query for the at least one candidate molecule;
creating, by the device, a k-dimensional tree graph based on the query for the at least one candidate molecule and based on the selected one or more points;
determining, by the device, a plurality of paths in the latent space according to an interpolation technique;
receiving, by the device, preference data;
determining, by the device, an optimum path from the plurality of paths based on the preference data;
determining, by the device, at least one candidate point on the optimum path; and
determining, by the device, a drug molecular structure for each of the at least one candidate point using an inverse of the grammar VAE model.

9. The method according to claim 8, further comprising:
obtaining, by the device, input data, the input data comprising a set of grammar rules and historical drug data; and
training, by the device, the grammar VAE model based on the input data.

10. The method according to claim 9, wherein:
the historical drug data comprises historical drug molecular structure data in a simplified molecular-input line-entry system (SMILES) data format;
the method further comprises:
   converting, by the device, the set of grammar rules into a one-hot encoding format, and
   converting, by the device, the historical drug data into the one-hot encoding format; and
training the grammar VAE model based on the input data comprises:
   training, by the device, the grammar VAE model based on the set of grammar rules in the one-hot encoding format and the historical drug molecular structure data in the one-hot encoding format.

11. The method according to claim 8, wherein:
the drug data comprises drug molecular structure data in a SMILES data format; and
the preference data comprises at least one expert-defined heuristics to be used to weight at least one path distance in the k-dimensional tree graph.

12. The method according to claim 8, wherein:
the query for the candidate molecule comprises a drug molecular structure query, and/or a drug treatment query, and/or a drug effect query.

13. The method according to claim 12, wherein selecting the one or more points in the latent space based on the query for the candidate molecule comprises:
   selecting, by the device, a first point in the latent space based on the drug treatment query according to a centroid algorithm;
   selecting, by the device, a second point in the latent space based on the drug molecular structure query according to a centroid algorithm; and
   determining, by the device, a plurality of paths between the first point and the second point in the latent space according to a Riemannian interpolation technique.

14. The method according to claim 8, further comprising:
receiving, by the device, a set of semantic rules; and
selecting, by the device, one or more candidate molecules from at least one candidate drug molecular structure based on the semantic rules.

15. A product comprising:
a non-transitory machine-readable media;
instructions stored on the machine-readable media for identify at least one candidate molecule; and
wherein when a processor executes the instructions, the product is configured to cause the processor to:
   receive drug data;
   convert the drug data into at least one point in a latent space using a grammar variational auto-encoder (VAE) model;
   receive a query for the at least one candidate molecule;
   select one or more points in the latent space based on the query for the at least one candidate molecule;
   create a k-dimensional tree graph based on the query for the at least one candidate molecule and based on the selected one or more points;

determine a plurality of paths in the latent space according to an interpolation technique;
receive preference data;
determine an optimum path from the plurality of paths based on the preference data;
determine at least one candidate point on the optimum path; and
determine a drug molecular structure for each of the at least one candidate point using an inverse of the grammar VAE model.

16. The product according to claim 15, wherein, when a processor executes the instructions, the product is configured to further cause the processor to:
obtain input data, the input data comprising a set of grammar rules and historical drug data; and
train the grammar VAE model based on the input data.

17. The product according to claim 16, wherein:
the historical drug data comprises historical drug molecular structure data in a simplified molecular-input line-entry system (SMILES) data format; and
when the processor executes the instructions, the product is configured to cause the processor to:
convert the set of grammar rules into a one-hot encoding format, and
convert the historical drug data into the one-hot encoding format; and
when the product is configured to cause the processor to train the grammar VAE model based on the input data, the product is configured to cause the processor to:
train the grammar VAE model based on the set of grammar rules in the one-hot encoding format and the historical drug molecular structure data in the one-hot encoding format.

18. The product according to claim 15, wherein:
the drug data comprises drug molecular structure data in a SMILES data format;
the preference data comprises at least one expert-defined heuristics to be used to weight at least one path distance in the k-dimensional tree graph; and
the query for the candidate molecule comprises a drug molecular structure query, and/or a drug treatment query, and/or a drug effect query.

19. The product according to claim 18, wherein, when the product is configured to cause the processor to select the one or more points in the latent space based on the query for the candidate molecule, the product is configured to cause the processor to:
select a first point in the latent space based on the drug treatment query according to a centroid algorithm;
select a second point in the latent space based on the drug molecular structure query according to a centroid algorithm; and
determine a plurality of paths between the first point and the second point in the latent space according to a Riemannian interpolation technique.

20. The product according to claim 15, wherein, when the processor executes the instructions, the product is configured to further cause the processor to:
receive a set of semantic rules; and
select one or more candidate molecules from at least one candidate drug molecular structure based on the semantic rules.

* * * * *